(12) United States Patent
Lordereau

(10) Patent No.: US 7,946,974 B2
(45) Date of Patent: May 24, 2011

(54) BIOMEDICAL DEVICE FOR TREATING BY VIRTUAL IMMERSION

(76) Inventor: Olivier Lordereau, Creancey (FR)

( * ) Notice: Subject to any disclaimer, the term of this patent is extended or adjusted under 35 U.S.C. 154(b) by 0 days.

(21) Appl. No.: 12/084,736

(22) PCT Filed: Nov. 10, 2006

(86) PCT No.: PCT/FR2006/051161
§ 371 (c)(1),
(2), (4) Date: Dec. 3, 2008

(87) PCT Pub. No.: WO2007/057601
PCT Pub. Date: May 24, 2007

(65) Prior Publication Data
US 2009/0137860 A1    May 28, 2009

(30) Foreign Application Priority Data

Nov. 10, 2005    (FR) .................................. 05 53435

(51) Int. Cl.
*A61M 21/00*    (2006.01)
(52) U.S. Cl. ........................... 600/27; 128/897; 434/236
(58) Field of Classification Search .............. 600/26–28; 128/897–898
See application file for complete search history.

(56) References Cited

U.S. PATENT DOCUMENTS

| | | | | |
|---|---|---|---|---|
| 5,046,494 A | * | 9/1991 | Searfoss et al. | 607/88 |
| 5,130,794 A | | 7/1992 | Ritchey | |
| 5,418,584 A | | 5/1995 | Larson | |
| 5,495,576 A | | 2/1996 | Ritchey | |
| 5,546,943 A | * | 8/1996 | Gould | 600/425 |
| 5,606,458 A | | 2/1997 | Fergason | |
| 5,883,606 A | | 3/1999 | Smoot | |
| 6,064,749 A | | 5/2000 | Hirota et al. | |

(Continued)

FOREIGN PATENT DOCUMENTS

JP    2004-298430 A    10/2004

(Continued)

OTHER PUBLICATIONS

"A Survey of Augmented Reality", R.T. Azuma; Hughes Research Laboratories, Malibu, CA., In Presence: Teleoperators and Virtual Environments 6, 4 (Aug. 1997), 355-385.

(Continued)

*Primary Examiner* — Charles A Marmor, II
*Assistant Examiner* — Carrie Dorna
(74) *Attorney, Agent, or Firm* — Harness, Dickey & Pierce, P.L.C.

(57) ABSTRACT

The invention relates to a biomedical device comprising computing means, immersion means for dipping a patient in a virtual intelligent environment, an interface for controlling the computing means, operating the immersion means and for collecting results of related medical means and different means for obtaining said results. The inventive device is characterized in that the computing means are used for controlling the immersion means in such a way that virtual three-dimensional therapeutic environments comprising a virtual person in the form of the patient, a closed three-dimensional envelop emitting at a determined light frequency which envelops the person and any scenery in which the virtual person and the closed radiating envelop thereof are located for receiving a determined psycho-neuro-immunologic response, which is positive for the organism, are formed. In particular the inventive method consists in progressively increasing the light frequency of the closed envelop and of the person receiving said radiation.

15 Claims, 2 Drawing Sheets

U.S. PATENT DOCUMENTS

| | | | |
|---|---|---|---|
| 6,124,825 | A | 9/2000 | Eschenbach |
| 6,278,479 | B1 | 8/2001 | Wilson et al. |
| 6,317,127 | B1 | 11/2001 | Daily et al. |
| 6,408,257 | B1 | 6/2002 | Harrington et al. |
| 6,425,764 | B1 | 7/2002 | Lamson |
| 6,702,767 | B1 | 3/2004 | Douglas et al. |
| 6,774,869 | B2 | 8/2004 | Biocca et al. |
| 2002/0075201 | A1 | 6/2002 | Sauer et al. |
| 2004/0024287 | A1 | 2/2004 | Patton et al. |
| 2005/0083248 | A1 | 4/2005 | Biocca et al. |
| 2007/0035563 | A1 | 2/2007 | Biocca et al. |

FOREIGN PATENT DOCUMENTS

| | | |
|---|---|---|
| WO | WO-99/06981 A | 2/1999 |
| WO | WO-99/27839 | 6/1999 |
| WO | WO-00/62850 A | 10/2000 |

OTHER PUBLICATIONS

"Hybrid Inertial and Vision Tracking for Augmented Reality REgistration", S. You, et al.; Integrated Media Systems Center, Univ. of Southern Califonia, L.A., CA.; HRL Laboratories, Malibu, CA., 1087-8270/99, 1999 IEEE, pp. 260-267.

"A Motion-Stabilized Outdoor Augmented Reality System", R. Azuma, et al., HRL Laboratories, Malibu, CA, 1087-8270/99, 1999 IEEE; pp. 252-259 and cover page.

"Basics of Integrated Information and Physical Spaces: The State of the Art", N.A. Streitz, et al., GMD-IPSI, German Nat'l Research Center for Information Technology, Darmstadt, Germany/Xerox PARC, Palo Alto, CA., ACM ISBN 1-58113-028-7; CHI 98 Apr. 18-23, 1998, Late-Breaking Results, pp. 273-274.

"Wearable Computers for Three Dimensional CSCW", M. Billinghurst, et al., Human Interfact Technology Laboratory, University of Washington, Seattle, WA., published prior to 2004.

* cited by examiner

BIOMEDICAL DEVICE FOR TREATING BY VIRTUAL IMMERSION

This present invention concerns a biomedical device using a special virtual three-dimensional environment intended to ease pain, to stimulate the immune system of a human being, to treat neuro-degenerative illnesses, to accelerate the process of cellular healing and to stabilise hair loss.

Currently, no biomedical technology is able to act directly and simultaneously on pain, the immune system, and a neuro-degenerative illness. Instead, people resort to individual technologies using the services of various specialist practitioners, leading to a very high social cost.

The device of the invention allows us to overcome this drawback.

To this end, the invention concerns a biomedical device that includes computing means, immersion means used to immerse a patient in an virtual intelligent environment, an interface used to control the computing means, to control the immersion means, and to collect the results of connected medical means, and the miscellaneous means to obtain these results, where the device is characterised by the fact that the computing means are arranged to control the immersion means and thereby to create three-dimensional therapeutic virtual environments that include a virtual character representing the patient, a closed three-dimensional envelope radiating at a given light frequency that envelopes the said character, a decor of some kind in which the virtual character is located, as well as its closed envelope radiating according to predetermined stages of a process, in order to obtain a therapeutic response, and a given psycho-neuro-immunological one in particular, that is positive for the organism.

More particularly, the said process includes a progressive raising of the said light frequency of the closed envelope and of the character that is receiving the said radiation.

By decor of some sort is meant a decor or an environment that can be either realistic, such as a verdant countryside or a beach leading down to the sea with a blue sky above, or an imaginary decor that makes reference to no realistic environment.

This process acts as a neuropsychological mechanism that allows the brain of the patient to identify with the virtual character, which could be described as a mirror effect.

The immersion means are preferably arranged to represent a virtual character whose gender is that of the patient.

According to one particular application, the device is intended to ease pain, and even the pain of phantom limbs.

This application has the advantage, in relation to more conventional methods, that it does not create significant side effects or addictions.

In the latter case, the control interface is arranged to control the computing means so as to amputate the limb of the said character, and the computing means are arranged, as a consequence, to represent the character with an amputated limb using the immersion means.

According to one particular decor, the immersion means are arranged to represent a three-dimensional scene illuminated by coloured lights of the same colour tones as the closed envelope, changing according to predetermined stages of the pre-established therapeutic process, in order to facilitate mental projection in the coloured closed envelope, with white being the only colour to remain invariant during the pre-established therapeutic process.

The immersion means are advantageously arranged to accelerate the healing process.

More particularly, the immersion means are arranged to represent a closed shape with a radiating outline of coloured lights of various intensities, centred around the virtual character, and changing according to the predetermined stages of the therapeutic process.

The invention will be better understood by reading the description that follows of a preferred form of implementation of the invention, with reference to the attached drawing in which.

Figure 1:
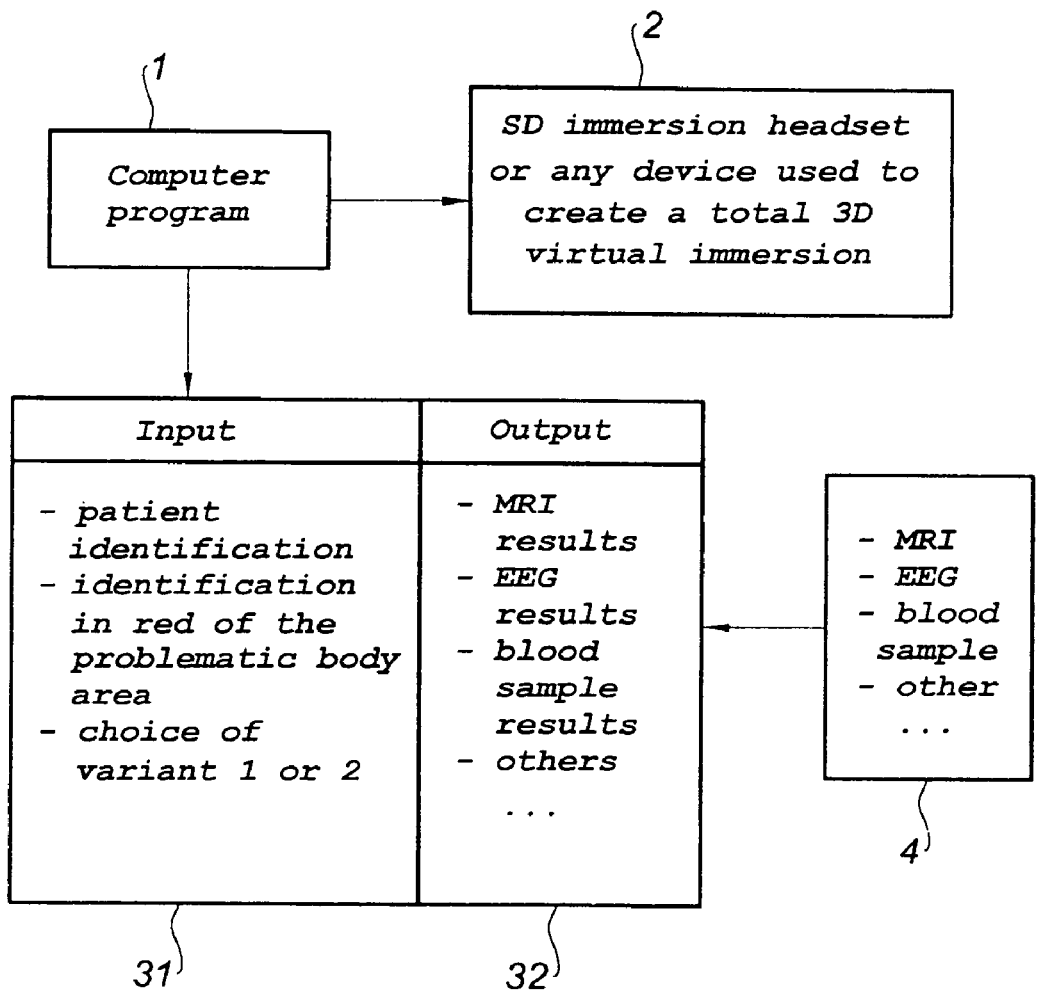
FIG. 1 represents a functional block diagram of the biomedical device of the invention.

Referring to FIG. 1, the biomedical device includes computing means 1, such as a computer that includes an ordinary computer operating program of an application for the generation of a three-dimensional (3D) geometrical environment in configurable colours, an immersion headset 2 in three dimensions, or any appliance that can be used to create a 3D virtual immersion effect, a control interface 31 that can be used to enter the identity of the patient and to indicate, by means of a red zone, the zone of the patient to be treated, and to display and record the results 32 on a magnetic or other medium, such as a DVD disk, and/or on paper, obtained from the magnetic resonance imaging (MRI), an electroencephalogram (EEG), or any other medical results proper to the patient treated.

The biomedical device also includes the miscellaneous means 4 ordinarily used to obtain the aforementioned MRI, EEG, etc. results.

The use of the device will now be explained.

A patient is invited to don the headset 2. On the interface 31, a practitioner enters the identity of the patient, his or her gender, the location of the affected zone of the patient, and the predetermined stages of the therapeutic process envisaged for the patient, with its parameters, such as the choice of dominant colours, and choice of therapeutic process.

The 3D application of the computer 1 creates a decor that includes a virtual stylised character as a man or woman seated on an armchair. This decor is composed, for example, of an armchair, in green tones, such as jade, a green and white ground, composed for example of jade tiles and white-coloured quartz forming the outlines. The decor can also include fountains, with green reflections shooting jets of green colour to a height that floods the decor in the same colours. The composition of this decor is designed to reinforce and facilitate the mental projection of immersing the patient in the closed envelope.

With this objective in mind, the decor can also include flowers and plants of various shapes and also in greenish colours, such as emerald for example. The scene also contains a jade stone for example, of oval shape and large size, that fills a good part of the decor, and at its apex rests a jade chalice, white in outline with a flat base, and holding an emerald flame.

The stylised character is surrounded by a three-dimensional envelope, closed like a shell, of oval, spherical or other shape, which fills a good part of the decor. This envelope gently radiates a different green colour from the jade shade, such as emerald tones, so as to stand out from the environment of jade green tones. The stylised character itself is of the same colour as the envelope, here an emerald green colour. All the outlines are drawn in white.

The purpose of this environment is to create a mirror effect in which the patient is looking at the stylised character which suffers from the same pathologies as he or she, as indicated by a red mark.

The gender of the stylised character is preferably the gender of the patient treated.

At the beginning of the session, the stylised character is represented naked with its skin texture. The envelope—the shell—is not activated, meaning that it does not appear. The zone to be treated is then activated by the practitioner by means of the interface 31. It is marked by a red zone. The decor is green.

An example of the process is as follows:

The shell forms a few seconds after activation of the zone to be treated, and the representation of the decor in green lasts for a given period, of 4 minutes for example.

Then the colour of the decor changes to blue shades for a preset time, like 2 minutes, and then the colour of the decor shifts to violet shades. During this session, the frequency of the light waves is thus increased.

In this last decor, the jade colour is replaced by amethyst and the emerald by a violet colour (lilac type). The "violet shell" stage lasts for 1 minute, radiating gently, and then intensifying its violet rays and transforming into a sort of violet flame for 5 minutes.

At the 12th minute, the flame transforms again into a violet shell that radiates gently.

At the 13th minute, the application returns to the blue decor, and then in the 14th minute, it returns to the green decor, and finally in the 15th minute, the virtual or stylised character comes back to its normal skin texture, with the red zone having disappeared.

There then remains a small violet flame at the centre of the stylised character, in order that the patient will know that the therapy is continuing its action on the body.

Execution of the aforementioned stages can be accompanied by the playing of an audio tape that can be used to introduce the patient, gently and safely, into the virtual environment.

The audio track in particular indicates to the patient that the violet flame does not burn and in fact is quite cold.

The device can include several modes of representation of the virtual environment:

The environment can include different green, blue or violet decors and colour tones.
The shell can be replaced by a flame or a sphere.
The length of the coloured stages and of the session can also be configured.

According to a first variant of the virtual environment, it is possible to help the patients suffering from phantom pain, meaning those with an amputated limb which continues to generate pain. By means of the interface 31, the practitioner is then able to control the application so that it calculates and controls the virtual environment in order to represent the stylised character that has lost the same limb as the patient concerned.

According to a second variant of the virtual environment, to the extent that this treatment stimulates the immune system, it is possible to help the patients suffering from an incipient baldness associated with a deficiency of the immune system, by stabilising the hair loss using the stylised character.

In this variant, the practitioner enters, via the interface 31, the zone at which the baldness is starting, and starts the application to create the stylised character with this baldness area marked in red. During the return stage to the moment when the stylised character comes back to its normal skin texture, the zone initially in red is totally covered with hair, the red zone having disappeared so as to indicate to the patient that the repair process is executing.

The device of the invention is particularly intended to treat people who suffer from pain or that have a poor immune system, so as to strengthen the latter, or that suffer from neuro-degenerative illnesses, or indeed to accelerate the healing process or stabilise hair loss.

It is according to the results obtained from the connected means 4 and displayed by the collection means 32 that the practitioner chooses the therapeutic process envisaged for the patient.

This technology, based on optoelectronics, stimulates the capacities of the human brain, and allows us, in time, to understand the role of the brain in the mechanisms of healing.

The virtual environment can contribute to enabling the brain to function in an optimal manner by creating a self-healing mechanism through the induction of a psycho-neuro-immunological response.

Two studies conducted on pain have shown that the "virtual reality" biomedical device in question here has the ability to reduce pain considerably, including those of a chronic character, without inducing any significant side effects.

The total length of a session during these studies was 17 minutes divided up as follows: the duration of the wavelengths used for the closed shape was 5 minutes, with the shell radiating at the frequency of the green colour, 3 minutes with the shell radiating at the frequency of the blue colour, and 5 minutes with the radiation at the frequency of violet (including the shell and the flame).

It should be noted that tests without using the radiating closed envelope have firmly indicated a smaller reduction in the pain.

Assessment of the Analgesic Properties of the "Virtual Reality" Biomedical Device on Delayed Onset Muscle Soreness.

An assessment has been made of the analgesic properties of the "virtual reality" biomedical device on Delayed Onset Muscle Soreness (DOMS) induced experimentally in healthy volunteering subjects. This muscular pain follows a progression in time that is characterised by the arrival of the first pain symptoms a few hours after the effort, and whose intensity increases gradually until a maximum is reached between 48 and 72 hours later. This pain then reduces progressively and finally disappears completely between the fifth and the seventh day following the exercise (Armstrong, 1984; Ebbeling & Clarkson, 1989; Miles & Clarkson, 1994). The objective of this study was to examine whether the main characteristics of the DOMS (change over time, intensity, etc.) could be influenced by a daily immersion of the subject in a virtual reality environment.

Eight healthy volunteers were asked to take part in this study, and after signature of their consent forms, to participate in a session of electro-stimulation (Electrical muscle stimulation (EMS) Compex Sport-P, at a frequency of 75 Hz) for a period of 13 minutes on the extensor muscles of the knee (on the non-dominant leg), and to undergo a session each day of immersion in the virtual environment for 17 minutes.

A previous study of the group had shown in fact that such a protocol resulted in a reduction of at least 20% in the maximum voluntary contraction (MVC) immediately after its execution (Zory et al., 2005) and gave rise to DOMS (Maffiuletti et al., 2006) that was similar to that observed conventionally after effort of the eccentric type. In this present study, we therefore propose to compare the intensity and the progression over 5 days of the DOMS seen previously, and therefore without recourse to the virtual reality device, with those that were noted on our subjects.

Beforehand, the maximum voluntary isometric force (MVIF) of the knee extensors of each subject was determined by means of a dynamometer (Biodex, Shirley Corporation, NY, USA). In like manner, the level of muscular pain was reported by each of the subjects on a 100 mm visual analogue scale (VAS). The pain intensity value (DOMS) obtained before the session (D0) were compared with those measured (D1) immediately after the EMS session, and then every 24 hours for 5 days (Session +24 hours=D2; +48 hours=D3, +72 hours=D4 and +96 hours=D5).

Figure 2:
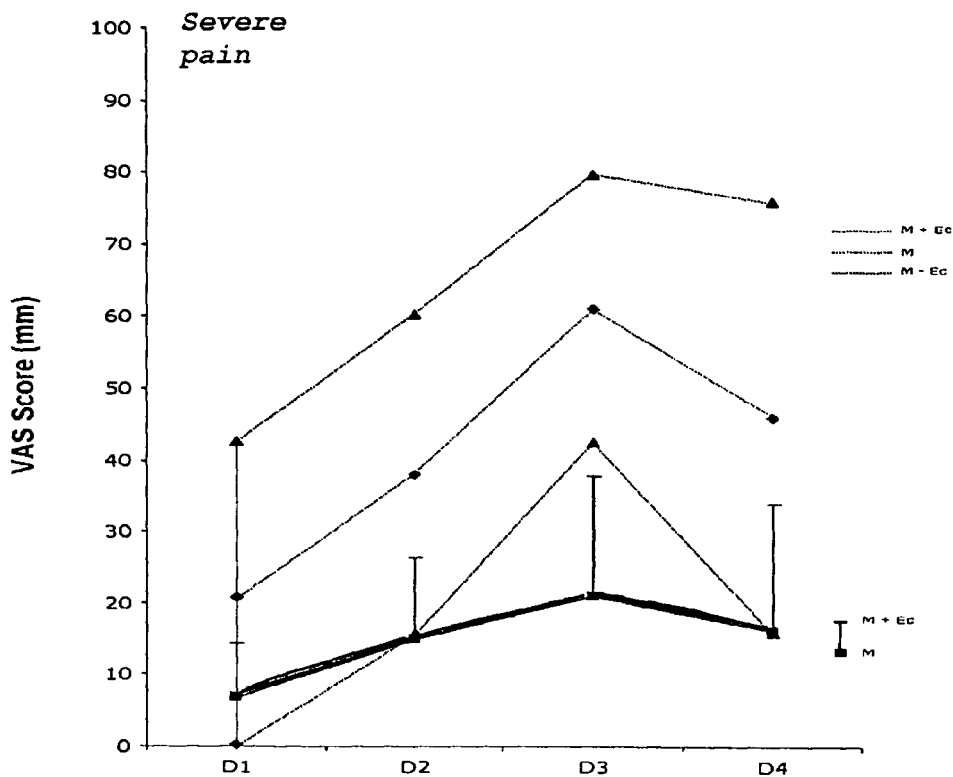
FIG. 2 is a graph showing changes in the muscular pain in the context of a first test.

In FIG. 2, the mean value (+/−Ec) of DOMS calculated on all of the eight subjects were reported (thin lines) for each of the measurement days (from D0 to D4) so as to observe their progression over time.

The progressive increase in the level of pain up to D3, followed by a reduction up to D4, is quite characteristic of DOMS, and also confirms the validity of such an EMS protocol for generating this type of muscular pain with delayed onset.

However, for its part, the intensity of the DOMS measured with virtual reality appears to be significantly lower than that obtained without virtual reality (thick lines), irrespective of the days of the measurement. This last result also shows that the virtual reality device used here is capable of reducing the intensity of the muscular pains generated by an EMS session.
Assessment of the Analgesic Effect of the "Virtual Reality" Biomedical Device on Chronic Pain This study proposed to assess the analgesic effect of the "virtual reality" biomedical device in volunteering subjects suffering from chronic pain.

The treatment was applied over a period of 4 weeks at the rate of 3 sessions per week, making a total of 12 sessions for each patient.

The 3 patients concerned were asked to evaluate their pain themselves on an analogue pain scale (the EVA scale) before starting the treatment (T0) and again at the end of the treatment (Tfin).

Figure 3:
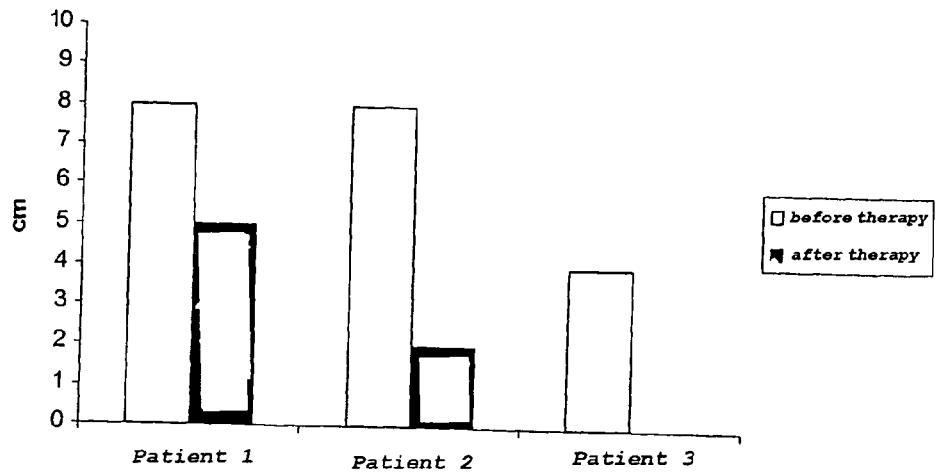
FIG. 3 is a graph showing a very significant reduction in chronic pain in the context of a second test.

On a pain scale of 0 to 10 centimeters, the pain assessment was as follows:
Analogue pain scale (EVA scale)
Patient 1 (75 years)
At T0: 8 cm
At Tfin (after 4 weeks of treatment): 5 cm
Patient 2 (48 years)
At T0: 8 cm
At Tfin (after 4 weeks of treatment): 2 cm
Patient 3 (58 ans)
At T0: 4 cm
At Tfin (after 4 weeks of treatment): 0 cm
The table in FIG. 3 summarises the results obtained.

A very significant reduction of the pain in the patients suffering from chronic pain was observed without creating any significant side effects.

In the context of the two tests, it has been possible to observe that there is no problem of toxicity, and that the volunteers in the two groups (the healthy volunteers and those suffering from chronic pain) all tolerated the virtual reality sessions very well. In the first group (the healthy volunteers), it was possible to observe over time a clear reduction in the pain that had been created artificially beforehand on the extensor muscles of the knee by electro-stimulation, in relation to a control group subjected to the same type of pain (DOMS or delayed-onset muscle soreness).

In the patients suffering from chronic pain, it was possible to observe a very significant reduction in the pain after 4 weeks of treatment. In conclusion, it is possible to say that the technology is effective in combating pain, including that of a chronic character, and that it allows us to treat the patients without generating any significant side effects or addictions.

In addition to the many applications that can be envisaged, in the sports area for example, and in particular in terms of physical preparation and recovery, as well as in the medical and therapeutic field, the technology used by this virtual reality device allows us to explore new investigative paths, located at the crossroads of many scientific disciplines, which could contribute rapidly to improving our understanding of the complex mechanisms that are responsible for pain.

REFERENCES

Armstrong, R. B. (1984). Mechanisms of exercise-induced delayed onset muscular soreness: a brief review. Med. Sci. Sports Exerc. December; 16(6):529538

Ebbeling C B & Clarkson P M. (1989). Exercise-induced muscle damage and adaptation. Sports Med. April; 7(4): 207-234

Miles M P & Clarkson P M. (1994). Exercise-induced muscle pain, soreness, and cramps. J Sports Med Phys Fitness. September; 34(3):203-216

Zory R & Boerio D & Jubeau M & Maffiuletti N A. (2005). Central and peripheral fatigue of the knee extensor muscles induced by electromyostimulation. Int J Sports Med. December; 26(10):847-853

Maffiuletti NA & Herrero A & Jubeau M & Bizzini M & Dvorak J. (2006). Gender differences in sensory and motor thresholds during electrical stimulation of the quadriceps femoris muscle. 11th annual ECSS-Congress, Lausanne (personal communication of the VAS data score for DOMS for our study).

The invention claimed is:

1. A biomedical method, comprising:
immersing a patient in a three-dimensional therapeutic virtual environment, wherein the environment includes:
a décor,
a virtual character representing the patient and being located in the décor;
an envelope having a closed three-dimensional shape, radiating at a given light frequency, the envelope being controlled to appear in the décor so that to envelop the virtual character;
radiating the décor at a light color of green; and
shifting the light color of the décor from green to blue and then shifting the light color of the décor from blue to violet in order to obtain a given psycho-neuro-immunological response that is positive for the patient.

2. A biomedical device, comprising:
immersion means used to immerse a patient in a virtual intelligent environment, computing means arranged to control the immersion means,
an interface used to control the computing means, wherein the computing means create three-dimensional therapeutic virtual environments that include:
a décor,
a virtual character representing the patient and being located in the décor;
an envelope having a closed three-dimensional shape, radiating at a given light frequency, the envelope being controlled to appear in the décor so that to envelop the virtual character;
the décor radiating according to predetermined stages in which the frequency of the color light waves of the décor is increased, in order to obtain a given psycho-neuro-immunological response that is positive for the patient.

3. The device according to claim 1, wherein the closed envelope and the character are radiating according to predetermined stages in which the frequency of the color light waves is increased.

4. The device according to claim 1, wherein the immersion means are arranged to represent the virtual character whose gender is that of the patient.

5. The device according to claim 4, wherein, the device being intended to ease the pain of phantom limbs, the interface is arranged to control the computing means so as to amputate the limb of the character, and the computing means are then arranged to represent the character with an amputated limb using the immersion means.

6. The device according to claim 1, arranged to greatly ease pain, including that of a chronic character.

7. The device according to claim 1, arranged to accelerate the healing process.

8. A biomedical device, comprising:
an immersion device operable to create three-dimensional therapeutic virtual environment for a patient, wherein the virtual environment includes:
a décor;
a virtual character representing the patient and being located in the décor;
an envelope having a closed three-dimensional shape, radiating at a given light frequency, the envelope being controlled to appear in the décor so that to envelop the virtual character;
wherein the décor radiates at a color shifting from green to blue and then from blue to violet in order to obtain a given psycho-neuro-immunological response that is positive for the patient;
a computer operably connected to the immersion device and configured to control the immersion device; and
an interface operably connected to the computer and configured to receive input regarding the patient.

9. A biomedical method, comprising:
immersing a patient in a three-dimensional therapeutic virtual environment, wherein the environment includes:
a décor;
a virtual character representing the patient and being located in the décor;
an envelope having a closed three-dimensional shape, radiating at a given light frequency, the envelope being controlled to appear in the décor so that to envelop the virtual character;
radiating the décor at a given light frequency; and
increasing the light frequency in order to obtain a given psycho-neuro-immunological response that is positive for the patient.

10. The method of claim 9 further comprises increasing the light frequency from green to blue and then to violet.

11. The method of claim 10 wherein it is used to ease pain or to treat pain, including that of a chronic character.

12. The method of claim 10 further comprises representing the virtual character with an amputated limb.

13. The method of claim 10 wherein it is used to accelerate a healing process.

14. The method of claim 9 further comprises representing the virtual character as gender of the patient.

15. The method of claim 9 further comprises radiating the closed envelope and the virtual character at the given frequency and progressively raising the light frequency of the closed envelope and the virtual character.

* * * * *